(12) United States Patent
Haeseler et al.

(10) Patent No.: US 6,706,531 B1
(45) Date of Patent: Mar. 16, 2004

(54) DEVICE FOR CONDITIONING A POLLUTED SOIL-SAMPLE-METHOD OF ANALYSIS BY PYROLYSIS

(75) Inventors: Franck Haeseler, La Garenne Colombes (FR); Yves Benoit, Saint Ouen l'Aumone (FR)

(73) Assignee: Institut Francais Du Petrole, Rueil-Malmaison Cedex (FR)

( * ) Notice: Subject to any disclaimer, the term of this patent is extended or adjusted under 35 U.S.C. 154(b) by 215 days.

(21) Appl. No.: 09/667,575

(22) Filed: Sep. 22, 2000

(30) Foreign Application Priority Data

Sep. 23, 1999 (FR) .............................. 99 11923

(51) Int. Cl.⁷ .............................................. G01N 33/00
(52) U.S. Cl. .................... 436/139; 436/143; 436/174; 436/176; 422/61; 422/68.1; 422/78
(58) Field of Search ..................... 422/61, 68.1, 69, 422/78; 436/60, 139, 143, 174, 177; 73/64.56, 864.51, 864.58

(56) References Cited

U.S. PATENT DOCUMENTS

| | | | | |
|---|---|---|---|---|
| 2,336,176 A | * | 12/1943 | Horvitz | 23/230 |
| 2,345,219 A | * | 2/1944 | Sanderson | 23/232 |
| 3,992,174 A | * | 11/1976 | Nakamura et al. | 55/67 |
| 4,352,673 A | | 10/1982 | Espitalie | 23/230 |
| 4,532,722 A | * | 8/1985 | Sax | 8/198 |
| 4,608,859 A | * | 9/1986 | Rockley | 73/153 |
| 4,699,002 A | * | 10/1987 | Rockley | 73/153 |
| 4,783,206 A | * | 11/1988 | Cullen et al. | 55/387 |
| 5,000,920 A | * | 3/1991 | Heckmann et al. | 422/60 |
| 5,044,860 A | * | 9/1991 | Norem et al. | 414/287 |
| 5,355,736 A | | 10/1994 | Skogley | 73/863.21 |
| 5,358,851 A | * | 10/1994 | Peck | 435/7.93 |
| 5,685,891 A | * | 11/1997 | Peltola | 71/9 |
| 5,698,774 A | | 12/1997 | Osmanski | 73/61.43 |
| 5,786,225 A | | 7/1998 | Lafargue | 436/147 |
| 5,922,974 A | | 7/1999 | Davison et al. | 73/864.74 |
| 6,019,823 A | * | 2/2000 | Tischler et al. | 96/108 |
| 6,096,563 A | * | 8/2000 | Hajizadeh et al. | 436/523 |
| 6,117,328 A | * | 9/2000 | Sikdar et al. | 210/640 |
| 6,117,682 A | * | 9/2000 | Lynn et al. | 436/29 |
| 6,187,581 B1 | * | 2/2001 | Sicotte et al. | 435/262 |
| 6,319,484 B1 | * | 11/2001 | Shore et al. | 423/245.1 |
| 6,397,658 B1 | * | 6/2002 | Villettaz et al. | 73/19.12 |

FOREIGN PATENT DOCUMENTS

| | | | |
|---|---|---|---|
| EP | 590932 | 4/1994 | |
| GB | 21612369 | 1/1986 | |
| WO | WO95/26944 | * 10/1995 | C05F/11/08 |

* cited by examiner

*Primary Examiner*—Jill Warden
*Assistant Examiner*—Dwayne K Handy
(74) *Attorney, Agent, or Firm*—Antonelli, Terry, Stout & Kraus, LLP

(57) ABSTRACT

The present invention relates to a device for conditioning a soil or rock sample polluted by hydrocarbons. It also allows conditioning of pure polluting products. The device comprises a receptacle (1) containing a soil or rock sample (3), and an adsorbent material (4a, 4b) for adsorbing hydrocarbons or derivatives. The soil, rock or pollutant sample is preferably surrounded by two adsorbent layers. The invention also relates to a method of analysis by pyrolysis of a soil or rock sample polluted by hydrocarbons wherein the device according to the invention is used.

9 Claims, 3 Drawing Sheets

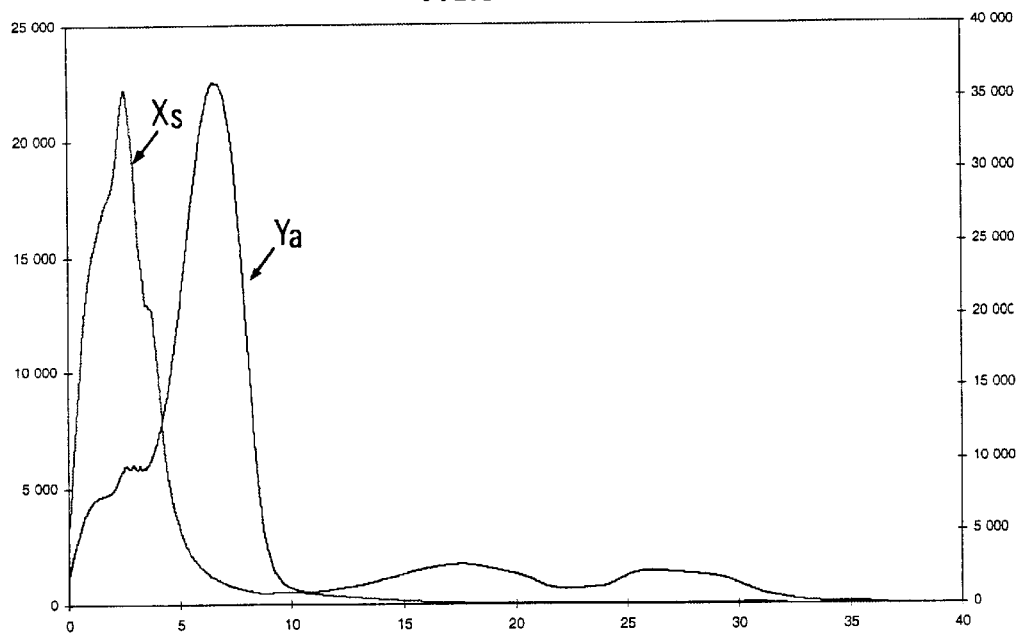
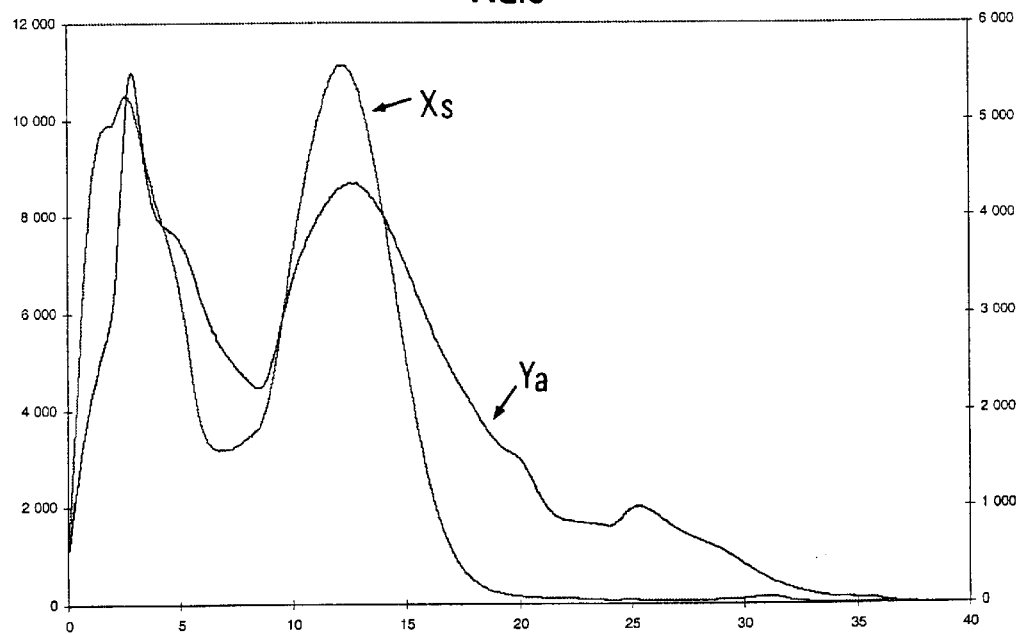

DEVICE FOR CONDITIONING A POLLUTED SOIL-SAMPLE-METHOD OF ANALYSIS BY PYROLYSIS

FIELD OF THE INVENTION

The present invention relates to a method and to a device for conditioning a rock, sediment or soil sample in order to determine, by pyrolysis, at least one pollution characteristic of a natural soil potentially or really contaminated by polluting products, notably hydrocarbons and/or derivatives. The invention also allows analysis of pure polluting products, tars, bitumens, etc., for example.

BACKGROUND OF THE INVENTION

For better comprehension, it can be reminded that:

during an accidental or chronic discharge (for example pipeline breakage, loss of tightness of a storage means, a tank for example, or after abandonment of ancient industrial sites), a certain amount of hydrocarbon compounds can seep into the soil, which causes pollution of all or part of said soil, knowledge of the type of pollutant (gasoline, kerosine, gas oil, lubricant, tars, bitumen, chlorine derivatives, . . . ) and knowledge of the extension in time and in space of the pollution is of great importance to people in charge of diagnosis, environmental impact studies and remediation of polluted soils. It is in fact well-known that the remediation techniques used depend on the type of polluting products.

It is therefore very important to quickly determine the nature of the pollutants and the quantity of soil to be treated, which directly depends on the extension of the pollution, at depth as well as at the surface. Determination of the degree of pollution of a soil allows to evaluate the volumes of ground to be treated, to determine the most suitable treating methods and the costs corresponding to the implementation thereof.

It then appears that systematic analysis of potentially or really polluted soil samples allows to quickly make a diagnosis concerning the nature and the extension of the pollution and the associated main risks (water table contamination for example).

In order to obtain reliable qualitative and/or quantitative analyses, it is generally necessary to subject samples of pure polluting products to pyrolysis.

Knowledge of such information allows to optimize operations of remediation of contaminated sites from the diagnosis stage. Without being totally suppressed, long and costly laboratory analyses are limited to the required minimum completing the information systematically collected by means of the method according to the present invention.

The ROCK-EVAL technique developed by the claimant, which is notably described in documents U.S. Pat. Nos. 4,153,415; 4,229,181; 4,352,673; 4,519,983, and in French patent application FR-94/08,383, is well-known. This method, which is fast, practically automatic, has been developed for characterization of mother rocks or reservoir rocks and of the hydrocarbons contained therein.

However, this method and the device are not totally suited for precise characterization of the various hydrocarbon cuts that can be contained in soils polluted by such products.

Document FR-2,753,271 describes an improvement of the ROCK-EVAL technique allowing more precise characterization of the pollutants, notably hydrocarbon and/or derivative type pollutants (chlorine, sulfur compounds, . . . ), contained in a polluted soil.

However, during analysis of polluted soils, the lighter polluting fractions, which can be related to gasoline and/or kerosine cuts with less than 12 carbon atoms, are very volatile. Although the baskets containing the sample to be analyzed can be inserted in a cooled sample changer, the volatile compound losses can exceed 90% in 24 hours. This is explained by the high vapour pressures of these light compounds and by the fact that the baskets containing the samples are not hermetically sealed.

SUMMARY OF THE INVENTION

The object of the present invention is consequently to limit or to suppress these evaporation losses, or to act on the evaporation rate.

The present invention thus relates to a device for conditioning a soil or rock sample polluted by hydrocarbons, or a hydrocarbon-based pollutant sample. The device comprises a receptacle containing the sample and a determined quantity of a material having the capacity to adsorb at least partly the hydrocarbons.

The sample can be surrounded in the receptacle by two adsorbent material layers.

The sample can be at least partly mixed with the adsorbent material.

The adsorbent product can consist of at least one of the following materials: silica, graphitized carbon, bentone, molecular sieve, clay.

The receptacle can comprise a bottom made of a gas porous material, a sintered metal for example.

The invention also relates to the method of analysis by pyrolysis of a soil or rock sample polluted by hydrocarbons, or of a hydrocarbon-based pollutant sample. This method uses the aforementioned device.

BRIEF DESCRIPTION OF THE DRAWINGS

Other features and advantages of the present invention will be clear from reading the description hereafter of non limitative examples, with reference to the accompanying figures wherein:

FIGS. 5 and 6 show, by way of comparison, the analysis of samples of two different rocks, with and without silica.

DETAILED DESCRIPTION

The device according to the prior art, described in document FR-2,753,271 mentioned here by way of reference, comprises a cooling system in the vicinity of the ramp of the sample baskets or sealed baskets.

The principle of the present invention is based on the effect of the addition of an adsorbent product, silica for example, to a soil or rock sample polluted by a light hydrocarbon fraction, the aim being to minimize light hydrocarbon evaporation losses by adsorbing these light fractions, for example on silica.

Figure 1:
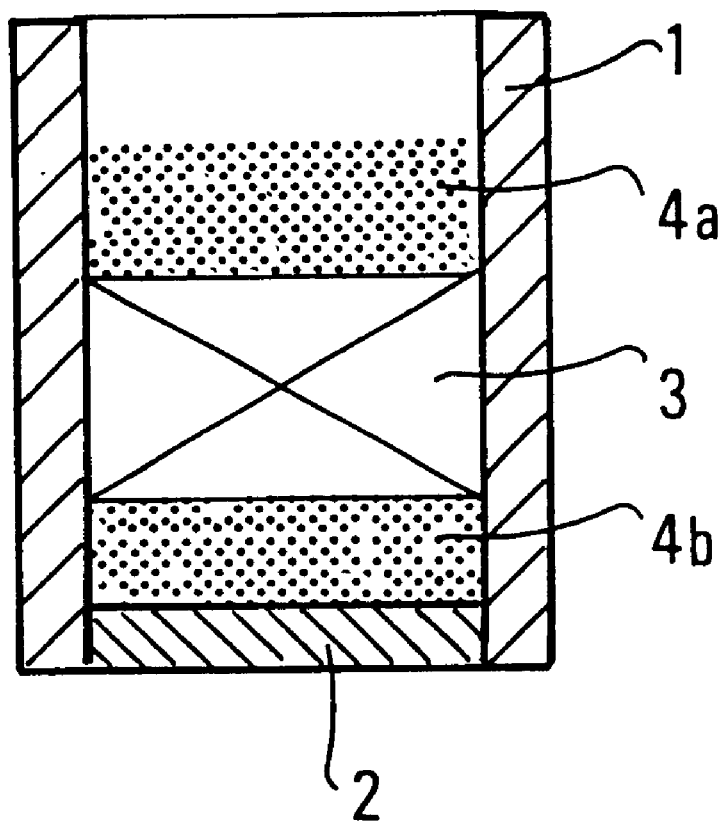
FIG. 1 is a sectional view of a basket used as a receptacle for the sample.

FIG. 1 is a sectional view of a basket consisting of a metallic cylinder 1 partly closed at the bottom by a sintered metal pellet 2. The bottom made of sintered material allows a carrier gas to flow through the basket so as to scavenge the materials placed in the basket. Sample volume 3 is surrounded by two silica layers 4a and 4b. The dimensions of the cylindrical basket are preferably: about 7 to 8 mm in diameter and 18 mm in height. The weight of the soil sample can range between 100 and 400 mg. Without departing from the scope of the present invention, there can be a mixture of the adsorbent material and of the polluted soil sample.

Tests

Figure 2:
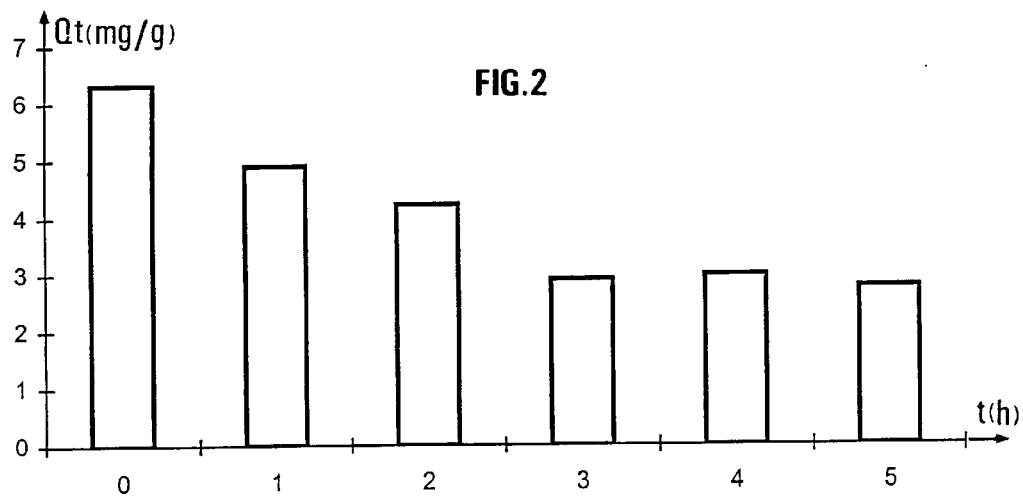
FIG. 2 illustrates an analysis carried out with a device according to the prior art.

Six baskets according to the prior art are identically filled with a homogenized sample of a soil polluted by gasoline type hydrocarbons, artificially enriched with kerosine (sample X). These. baskets are simultaneously placed on the conveyor of the device as described in document FR-2,753,271. Their content is analyzed at regular time intervals t (about 1 hour). The criterion observed is the total hydrocarbon concentration Qt of the sample (in mg/g). This value is representative of the lighter fractions, sample X containing only gasoline and kerosine. The results are given in FIG. 2. This figure shows a hydrocarbon loss of the order of 20% per hour. The analysis carried out in the POLLUT-EVAL device is therefore not representative from a quantitative point of view. Besides, from a qualitative point of view, this loss can lead to a wrong conclusion concerning the contaminating source.

Figure 3:
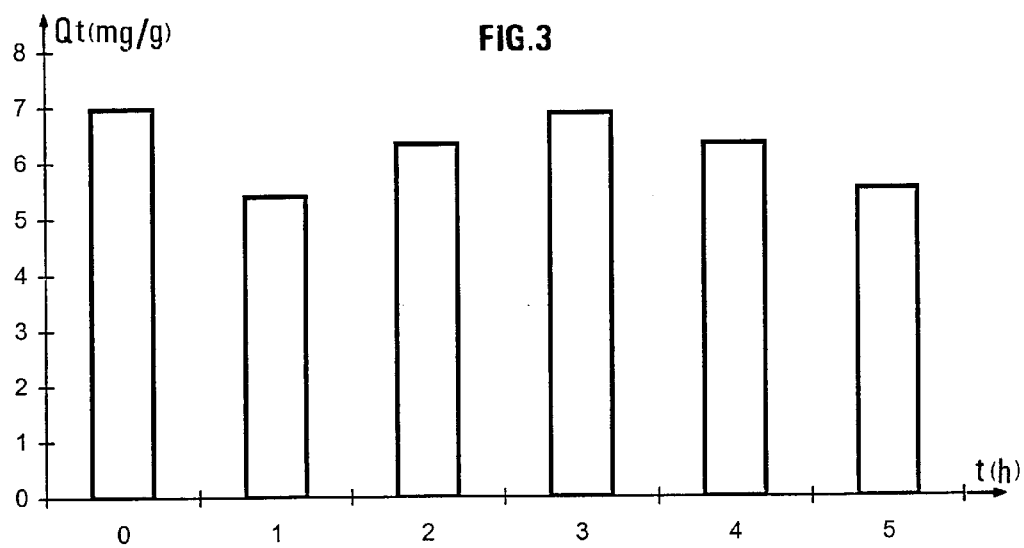
FIG. 3 illustrates an analysis carried out with the device and according to the method of the present invention.

Six baskets similar to the previous ones are prepared with the same polluted soil sample X. The sample is placed on a silica layer and covered with another silica layer. The baskets are simultaneously placed on the conveyor of the measuring device. The measuring cycle is carried out according to the previous test. FIG. 3 shows the retention effect of silica leading to a hydrocarbon concentration that remains stable with time. These results show that addition of silica in the receptacle solves the problem posed by keeping the light hydrocarbons in the soil sample.

Figure 4:
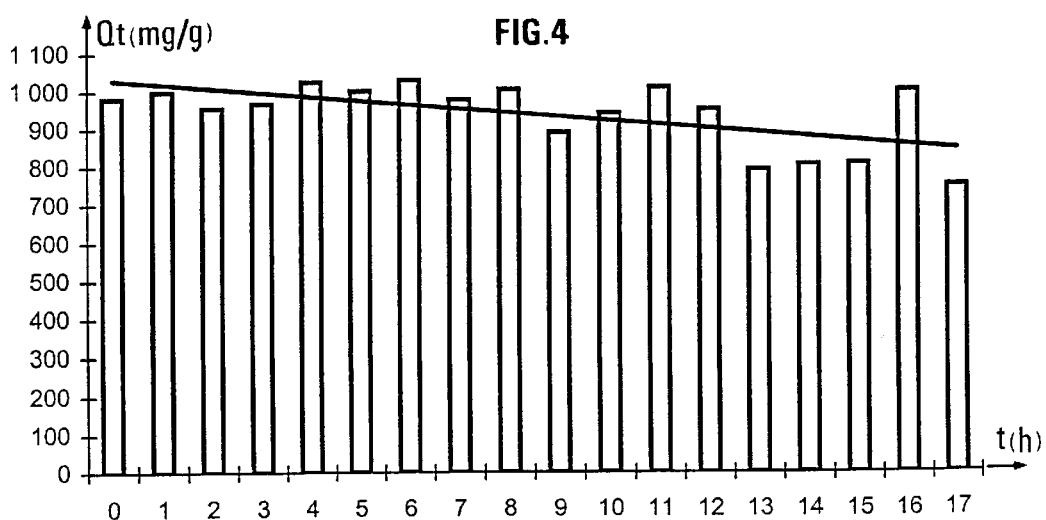
FIG. 4 illustrates an analysis similar to the previous one, but carried out for a greater length of time.

The effect of the silica in the baskets has been studied over a longer period. The same test as before has been carried out from 17 baskets comprising silica, whose content is analyzed every hour. The results given in FIG. 4 show no or only few losses during the first 12 hours. Silica is a solution to the problem of volatile compounds analysis.

All these results show that addition to a soil sample polluted by hydrocarbons of a material likely to adsorb and to trap the more volatile hydrocarbons allows to obtain optimized analyses by pyrolysis.

Of course, the effect of the retention by adsorption of the hydrocarbons has consequences on the profiles of the various peaks $Q_0, Q_1, Q_2, Q_3 \ldots$ measured by a POLLUT-EVAL type device. These drifts can however be taken into account by the analysis programs allowing to obtain qualitative and quantitative results.

This hydrocarbon retention effect allows, among other things, to obtain a pyrogram profile representative of the pollutant without being disturbed by the matrix effect, i.e. the more or less great retention of rocks. FIG. 5 shows two pyrograms Xs and Ya (the time is laid off as abscissa and the response of the FID detectors is laid off as ordinate). Xs is a sample of a polluted sandy soil and Ya is a sample of a clay soil. Reading the two pyrograms of FIG. 5 might lead to deduce that the two samples are polluted by different products. The same polluting product has however been used to prepare samples Xs and Ya. This gap is due to the difference of retention of the light hydrocarbons between the sandy soil and the clay soil.

FIG. 6 shows, for the same samples Xs and Ya analyzed according to the present invention, i.e. in the presence of adsorbent product in the baskets, a coincidence of the pyrograms, therefore that the polluting products of samples Xs and Ya are the same or are very close. Qualitative evaluation of the pollutant is thus much more representative with the present invention.

The invention is not limited to silica as the adsorbent; molecular sieves, graphitized carbons, bentone, clays or other products having the capacity to adsorb hydrocarbons or derivatives can also be used.

The invention is not limited to pollutant-impregnated soil or rock samples, it is clear that the present invention can be applied to analysis of more or less pure products such as tars, bitumens.

What is claimed is:

1. A method of analysis by pyrolysis of a soil or rock sample polluted by hydrocarbons or a hydrocarbon-based pollutant sample, comprising the steps of:

providing the soil or rock sample and a determined amount of an adsorbent material in a receptacle, the determined amount of adsorbent material having the capacity to adsorb at least part of the hydrocarbons to minimize evaporation losses thereof;

subjecting the hydrocarbons polluting the soil or rock sample to pyrolysis in the receptacle; and analyzing the hydrocarbons polluting the soil or rock sample.

2. A method as claimed in claim 1, wherein the step of adding to the receptacle a predetermined amount of an adsorbent material comprises surrounding the sample by two adsorbent material layers.

3. A method as claimed in claim 1, wherein the step of adding to the receptacle a predetermined amount of an adsorbent material comprises at least partly mixing the adsorbent material with the sample.

4. A method as claimed in claim 1, wherein the adsorbent material comprises at least one member selected from the group consisting of silica, graphitized carbon, bentone, molecular sieve, and clay.

5. A method as claimed in claim 1, wherein the receptacle comprises a bottom made of a gas porous material.

6. A method as claimed in claim 1, wherein the receptacle has metallic sidewalls and a bottom comprising a gas porous material.

7. A method as claimed in claim 6, wherein the sidewalls of the receptacle comprise a metallic cylinder and the bottom comprises a sintered metal pellet.

8. A method as claimed in claim 7, wherein the metallic cylinder has a diameter of about 7 to 8 mm.

9. A method as claimed in claim 1, wherein the sample has a weight in the range of 100 to 400 mg.

* * * * *